United States Patent [19]

Iwasaki et al.

[11] 4,298,530
[45] Nov. 3, 1981

[54] PROCESS FOR PRODUCTION OF 3-HYDROXY-3-METHYLPHTHALIDE OR THE NUCLEARLY SUBSTITUTED DERIVATIVES THEREOF

[75] Inventors: Hirokazu Iwasaki, Kawasaki; Hideo Takahashi, Ebina, both of Japan

[73] Assignee: Showa Denko K.K., Tokyo, Japan

[21] Appl. No.: 155,083

[22] Filed: Jun. 2, 1980

[30] Foreign Application Priority Data

Jun. 6, 1979 [JP] Japan .................................. 54-70153

[51] Int. Cl.³ .......................................... C07D 307/88
[52] U.S. Cl. ............................... 260/343.3 R; 562/459
[58] Field of Search .................. 260/343.3 R; 562/459

[56] References Cited

FOREIGN PATENT DOCUMENTS 50-70377  6/1975  Japan .
50-70378  6/1975  Japan .
50-84563  7/1975  Japan .

OTHER PUBLICATIONS

Finkelstein et al., J. Org. Chem., vol. 32, p. 3229.
Yale, J. Ameri. Chem. Soc. vol. 69, p. 1547.

*Primary Examiner*—Henry R. Jiles
*Assistant Examiner*—Jane T. Fan
*Attorney, Agent, or Firm*—Wenderoth, Lind & Ponack

[57] ABSTRACT

A process for producing 3-hydroxy-3-methylphthalide or its nuclearly substituted derivative of the following general formula

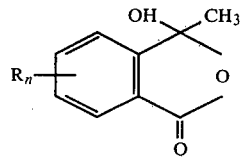

wherein R represents a lower alkyl group, a lower alkoxy group, a lower alkoxycarbonyl group or a carboxyl group, and n is 0 or an integer of 1 to 3, which comprises reacting phthalic anhydride or its nuclearly substituted derivative of the following general formula

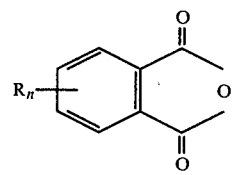

wherein R and n are as defined, with malonic acid at an elevated temperature in at least one solvent selected from the group consisting of dialkylformamides, dialkylsulfoxides and aliphatic lower carboxylic acids in the presence of, as a catalyst, a salt of an inorganic or organic acid with a metal selected from the group consisting of metals of Groups IA, IIA, IIIB and VIII of the periodic table, manganese, copper and zinc.

8 Claims, No Drawings

PROCESS FOR PRODUCTION OF 3-HYDROXY-3-METHYLPHTHALIDE OR THE NUCLEARLY SUBSTITUTED DERIVATIVES THEREOF

This invention relates to a process for producing 3-hydroxy-3-methylphthalide or its nuclearly substituted derivative of the general formula

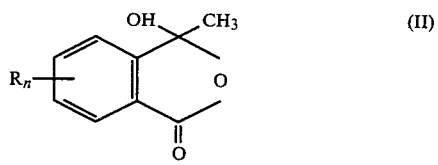

wherein R represents a lower alkyl group, a lower alkoxy group, a lower alkoxycarbonyl group or a carboxyl group, and n is O or an integer of 1 to 3, which comprises reacting phthalic anhydride or its nuclearly substituted derivative of the general formula

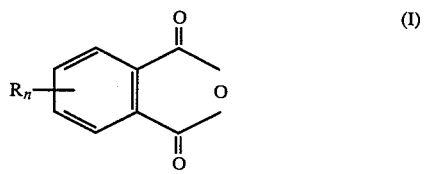

wherein R and n are as defined above,
with malonic acid in an organic solvent at an elevated temperature.

In the present specification and claims, the lower alkyl or lower alkoxy groups mean those having 1 to 4 carbon atoms.

The 3-hydroxy-3-methylphthalide or its nuclearly substituted derivatives of general formula (II) are useful as intermediates for synthesis of medicines, agricultural chemicals and other organic compounds. For example, 5,7-dimethyl-6-ethoxycarbonyl-3-hydroxy-3-methyl phthalide is used as an intermediate for synthesizing 6,8-dimethyl-7-ethoxycarbonyl-4-hydroxymethyl-1-phthalazone which is effective for prevention of arteriosclerotic diseases and thrombotic diseases (see Japanese Laid-Open Patent Publications Nos. 70377/75 and 70378/75).

It is known that as shown by the following formula, 3-hydroxy-3-methylphthalide of general formula (II) is in a tautomeric relationship with a compound of general formula (II) having a 2-acetylbenzoic acid structure, and depending upon conditions, either one of these structures is assumed (see, for example, J. Org. Chem., Vol. 32, page 3229).

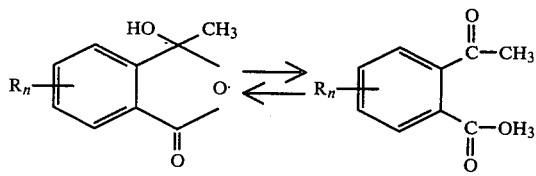

In the following description, however, compounds of general formula (II) are consistently termed 3-hydroxy-3methylphthalide or its substituted derivatives for the sake of convenience.

Synthesis of 3-hydroxy-3-methylphthalide by reacting phthalic anhydride with malonic acid in pyridine at an elevated temperature is well known as the Knoevenagel-Doebner method (see, for example, J. Am. Chem. Soc., Vol. 69, page 1547). This method is also applicable to the synthesis of 5,7-dimethyl-6-ethoxycarbonyl-3-hydroxy-3-methylphthalide, i.e. its nuclearly substituted derivative (see Japanese Laid-Open Patent Publication No. 84563/75).

When this method is practiced on an industrial scale, decomposition of the starting malonic acid in the pyridine solvent is vigorous, and therefore, malonic acid must be used in a considerably large excess. In particular, in the synthesis of a compound having substituents at asymmetric positions, for example 5,7-dimethyl-6-ethoxycarbonyl-3-hydroxy-3-methylphthalide as mentioned above, large amounts of compounds of a similar structure such as 4,6-dimethyl-5-ethoxycarbonyl-3-hydroxy-3-methylphthalide inevitably occur as by-products. Accordingly, in addition to the aforesaid difficulty, this method also poses a problem in the selectivity of the final desired product, its separation and purification, etc. and has not proved to be entirely satisfactory.

The present invention made extensive investigations about a process for synthesizing 3-hydroxy-3-methylphthalide or its nuclearly substituted derivatives with industrial advantage by reacting phthalic acid or its nuclearly substituted derivative with malonic acid. These investigations have led to the discovery that such a process can be performed with industrial advantage by performing the reaction in the presence of a specified catalyst in a specified organic solvent.

Thus, according to this invention, there is provided a process for producing 3-hydroxy-3-methylphthalide or its nuclearly substituted derivative of the general formula

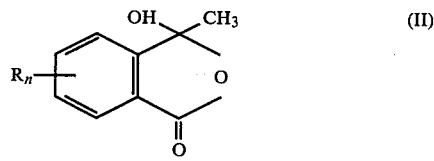

wherein R and n are as defined hereinabove,
which comprises reacting phthalic anhydride or its nuclearly substituted derivative of the general formula

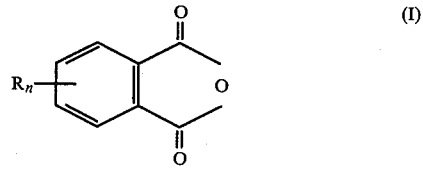

wherein R and n are as defined,
with malonic acid at an elevated temperature in at least one solvent selected from the group consisting of dialkylformamides, dialkylsulfoxides and aliphatic lower carboxylic acids in the presence of, as a catalyst, a salt of a metal selected from the group consisting of metals of Groups IA, IIA, IIIB and VIII of the periodic table, manganese, copper and zinc.

Examples of the starting material of formula (I) used in the process of this invention include phthalic anhydride, 3-methyl-phthalic anhydride, 3,4-dimethylphthalic anhydride, 3,4,5-trimethyl-phthalic anhydride, 3-methyl-4-ethyl-phthalic anhydride, 3,5-dimethyl-4-ethyl-phthalic anhydride, 4-carboxyphthalic anhydride, 4-ethoxycarbonylphthalic anhydride, 4-t-butoxycarbonylphthalic anhydride, 3-methyl-4-propoxycarbonylphthalic anhydride, 3,5-dimethyl-4-methoxycarbonylphthalic anhydride, 3,5-dimethyl-4-ethoxycarbonylphthalic anhydride, 3-methyl-4,5-diethoxycarbonylphthalic anhydride, 3-methoxyphthalic anhydride, 3,4-dimethoxy-phthalic anhydride, 4,5-dimethoxy-phthalic anhydride, and 4-t-butoxy-phthalic anhydride. From these compounds, the corresponding compounds of general formula (II) can be synthesized.

Organic solvents used for smooth proceeding of a reaction are required to be stable under the reaction conditions with no tendency to react with, or decompose, starting materials and the desired product, and to be capable of completely dissolving the starting materials and a catalyst. In the process of this invention, dialkylformamides, dialkylsulfoxides and aliphatic lower carboxylic acids have been found to be especially effective. Some typical examples of such organic solvents are N,N-dimethylformamide (DMF), N,N-diethylformamide, dimethylsulfoxide (DMSO), acetic acid (AcOH) and propionic acid.

The salts of the aforesaid metals used as a catalyst are usually salts of the metals with inorganic acids such as hydrohalic acids, sulfuric acid, nitric acid, phosphoric acid and carbonic acid, and salts of the metals with organic acids such as acetic acid, propionic acid, naphthenic acid, oxalic acid and benzoic acid. Examples of especially effective metal salts are lithium acetate, sodium formate, sodium acetate, sodium benzoate, sodium phosphate, sodium carbonate, potassium acetate, cesium carbonate, magnesium chloride, magnesium sulfate, magnesium acetate, calcium acetate, strontium chloride, barium diorthophosphate, yttrium chloride, manganese chloride, ferric chloride, cobalt acetate, nickel acetate, palladium acetate, cuprous chloride and zinc acetate. Unstable salts which are decomposed under the reaction conditions or are hydrolyzed or degenerated by traces of unavoidable moisture, etc. included in the reaction system, and insoluble salts which do not at all dissolve in the reaction system cannot be used because they do not exhibit the desired catalytic effect.

The mole ratio between the starting materials may be stoichiometric (i.e., the mole ratio is 1). Since, however, malonic acid is partly decomposed under the reaction conditions, it is preferred to use malonic acid in a slight excess. Usually, 1 to 10 moles, preferably 1.2 to 3.0 moles, of malonic acid is used per mole of phthalic anhydride or its nuclearly substituted derivative. The catalyst is generally more effective when used in a larger amount, but beyond a certain limit, no further increase in effect can be obtained. It is generally desirable to use the catalyst in an amount of 0.01 to 1.0 mole per mole of the phthalic anhydride or its nuclearly substituted derivative. The reaction temperature is usually 60° to 130° C., preferably 90° to 120° C. If the reaction temperature is at least 140° C., decomposition of the starting malonic acid is vigorous, and the yield of the product decreases extremely. On the other hand, at too low temperatures, the reaction time is prolonged, and no practical benefit is obtained. The reaction time varies depending upon various conditions such as the mole ratio between the starting materials, the concentration of the catalyst, and the reaction temperature. Under ordinary conditions, a reaction time of 5 to 20 hours leads to satisfactory yields of the final product.

The following Examples illustrate the process of this invention. It should be noted however that these Examples are merely illustrative, and do not in any way limit the scope of the present invention. The conversions and yields given in these Examples are based on the starting phthalic anhydride or its nuclearly substituted derivative.

EXAMPLE 1

A 300 ml. three-necked glass flask equipped with a reflux condenser, a thermometer and a stirrer was charged with a mixture consisting of 30 g of phthalic anhydride, 31 g of well-dried malonic acid, 19 g of magnesium chloride and 80 g of dimethylsulfoxide. The flask was heated in an oil bath, and phthalic anhydride was reacted with malonic acid at 90° to 95° C. for 8 hours with stirring.

After the reaction, the reaction mixture was analyzed by high-speed liquid chromatography. The conversion was 85%, and the yield of the desired 3-hydroxy-3-methylphthalide was 81%.

The reaction mixture was allowed to cool, and then with stirring, a 2 N aqueous solution of sodium hydroxide was added. Dimethylsulfoxide was removed by extraction with isopropyl ether. Hydrochloric acid was added to the aqueous layer until its pH reached 3.0. The crystals which precipitated were washed with water, and dried to afford 24 g of 3-hydroxy-3-methylphthalide having a purity, measured by liquid chromatography, of 99.7%.

EXAMPLE 2

A 500 ml. three-necked glass flask equipped with a reflux condenser, a thermometer and a stirrer was charged with a mixture consisting of 50 g of 3,5-dimethyl-4-ethoxycarbonyl-phthalic anhydride, 42 g of well-dried malonic acid, 30 g of sodium acetate and 200 g of acetic acid, and the flask was heated in an oil bath. The phthalic anhydride derivative was reacted with malonic acid at 90° to 95° C. for 15 hours with stirring. After the reaction, the reaction mixture was analyzed by high-speed liquid chromatography. It was found that the conversion was 90%, and the desired 5,7-dimethyl-6-ethoxycarbonyl-3-hydroxy-3-methylphthalide was obtained in a yield of 77%.

The reaction mixture was allowed to cool, and with stirring, 400 g of water was added. The resulting crystals were washed with water and dried to afford 35 g of 5,7-dimethyl-6-ethoxycarbonyl-3-hydroxy-3-methylphthalide having a purity, determined by liquid chromatography, of 99.5% and a melting point of 146° to 147° C.

EXAMPLES 3 TO 18

The procedure of Example 1 was repeated except as noted in Table I below. The results are also shown in Table 1.

TABLE 1

| Example | Catalyst Type | Amount (g) | Solvent | Temperature (°C.) | Time (hr) | Conversion (%) | Yield (%) |
|---|---|---|---|---|---|---|---|
| Control | None | — | DMSO | 90 | 24 | 0 | 0 |
| 3 | AcONa | 16 | " | " | 8 | 83 | 79 |
| 4 | AcOK | 20 | " | " | " | 78 | 74 |
| 5 | Na₂CO₃ | 21 | " | " | 12 | 68 | 65 |
| 6 | BaHPO₄ | 47 | " | " | " | 66 | 63 |
| 7 | HCOONa | 14 | " | " | " | 73 | 70 |
| 8 | ⟨◯⟩—COONa | 29 | " | " | " | 71 | 68 |
| 9 | SrCl₂ | 48 | " | " | " | 59 | 56 |
| 10 | (AcO)₂Zn | 55 | " | " | " | 63 | 60 |
| Control | None | — | DMF | 90 | 24 | 0 | 0 |
| 11 | MgCl | 19 | " | " | 8 | 84 | 80 |
| 12 | (AcO)₂Mg | 28 | " | " | " | 65 | 61 |
| 13 | AcONa | 16 | " | " | " | 85 | 81 |
| Control | None | — | AcOH | 90 | 24 | 0 | 0 |
| 14 | AcONa | 16 | " | " | 18 | 73 | 69 |
| 15 | AcOK | 20 | " | " | " | 68 | 65 |
| 16 | MgCl₂ | 19 | " | " | " | 59 | 56 |
| 17 | HCOONa | 14 | " | " | " | 69 | 66 |
| 18 | ⟨◯⟩—COONa | 29 | " | " | " | 65 | 61 |

Note:
Ac in the above table stands for CH₃CO.

EXAMPLES 19 TO 40

The procedure of Example 2 was repeated except as noted in Table 2 below. The results are also shown in Table 2.

TABLE 2

| Example | Catalyst Type | Amount (g) | Solvent | Temperature (°C.) | Time (hr) | Conversion (%) | Yield (%) |
|---|---|---|---|---|---|---|---|
| Control | None | — | DMSO | 90 | 24 | 0 | 0 |
| 19 | AcOLi | 8 | " | " | 8 | 87 | 67 |
| 20 | AcONa | 18 | " | " | " | 95 | 74 |
| 21 | AcOK | 20 | " | " | " | 90 | 70 |
| 22 | Cs₂CO₃ | 35 | " | " | " | 89 | 67 |
| 23 | MgCl₂ | 19 | " | " | " | 91 | 82 |
| 24 | (AcO)₂Ca | 32 | " | " | 20 | 80 | 70 |
| 25 | SrCl₂ | 48 | " | " | " | 82 | 71 |
| 26 | MnCl₂ | 25 | " | " | " | 91 | 81 |
| 27 | FeCl₃ | 33 | " | " | " | 74 | 66 |
| 28 | (AcO)₂Co | 35 | " | " | " | 76 | 68 |
| 29 | (AcO)₂Ni | 35 | " | " | " | 69 | 61 |
| 30 | (AcO)₂Pd | 45 | " | " | " | 63 | 52 |
| 31 | CuCl | 20 | " | " | 8 | 84 | 75 |
| Control | None | — | DMF | 90 | 24 | 0 | 0 |
| 32 | Cs₂CO₃ | 35 | " | " | 12 | 78 | 61 |
| 33 | MgCl₂ | 19 | " | " | 8 | 79 | 70 |
| 34 | YCl₃ | 39 | " | " | " | 62 | 57 |
| 35 | AcONa | 18 | " | " | " | 81 | 69 |
| Control | None | — | AcOH | 90 | 24 | 0 | 0 |
| 36 | AcOK | 40 | " | " | 15 | 88 | 76 |
| 37 | MgCl₂ | 19 | " | 95 | 12 | 85 | 76 |
| 38 | (AcO)₂Ca | 48 | " | " | " | 74 | 63 |
| 39 | HCOONa | 14 | " | " | " | 72 | 66 |
| 40 | ⟨◯⟩—COONa | 29 | " | " | " | 67 | 58 |

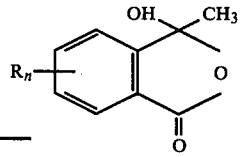

(II)

What we claim is:
1. In the process for producing 3-hydroxy-3-methylphthalide or its nuclearly substituted derivative of the formula wherein R represents a lower alkyl group, a lower alkoxy group, a lower alkoxycarbonyl group or a carboxyl group, and n is O or an integer of 1 to 3, by the reaction of phthalic anhydride or its nuclearly substituted derivative of the formula

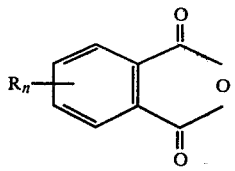

wherein R and n are as defined,
with malonic acid at a temperature of 60° to 130° C., the improvement according to which the reaction is carried out in at least one solvent selected from the group consisting of dialkylformamides, dialkylsulfoxides and aliphatic lower carboxylic acids in the presence of, as a catalyst, a salt of an inorganic or organic acid with a metal selected from the group consisting of metals of Groups IA, IIA, IIIB and VIII of the periodic table, manganese, copper and zinc.

2. The process of claim 1 wherein the solvent is N,N-dimethylformamide, N,N-diethylformamide, dimethylsulfoxide, acetic acid or propionic acid.

3. The process of claim 1 wherein said catalyst is lithium acetate, sodium formate, sodium acetate, sodium benzoate, sodium phosphate, sodium carbonate, potassium acetate, cesium carbonate, magnesium chloride, magnesium sulfate, magnesium acetate, calcium acetate, strontium chloride, barium diorthophosphate, yttrium chloride, manganese chloride, ferric chloride, cobalt acetate, nickel acetate, palladium acetate, cuprous chloride, or zinc acetate.

4. The process of claim 1 wherein said reaction is carried out at a temperature of 60° to 130° C.

5. The process of claim 1 wherein said reaction is carried out at a temperature of 90° to 120° C.

6. The process of claim 1 wherein the mole ratio of phthalic anhydride or its nuclearly substituted derivative to malonic acid is from 1:1 to 1:10.

7. The process of claim 1 wherein the mole ratio of phthalic anhydride or its nuclearly substituted derivative to malonic acid is from 1:1.2 to 1:3.0.

8. The process of claim 1 wherein the amount of said catalyst is 0.01 to 1.0 mole per mole of phthalic anhydride or its nuclearly substituted derivative.

* * * * *